United States Patent [19]

Tang et al.

[11] Patent Number: 4,503,226

[45] Date of Patent: Mar. 5, 1985

[54] PROCESS FOR TRIMERIZING ORGANIC POLYISOCYANATES

[75] Inventors: Kuo-Chang Tang, New Haven; Phillip T. Berkowitz, Woodbridge, both of Conn.

[73] Assignee: Olin Corporation, Cheshire, Conn.

[21] Appl. No.: 605,050

[22] Filed: Apr. 30, 1984

[51] Int. Cl.$^3$ .......................................... C07D 251/34
[52] U.S. Cl. ................................................. 544/193
[58] Field of Search ..................... 544/193; 528/423; 524/101

[56] References Cited

U.S. PATENT DOCUMENTS

| | | | |
|---|---|---|---|
| 3,954,684 | 5/1976 | Farrissey et al. | 260/2.5 |
| 3,980,594 | 9/1976 | Fabris et al. | 260/2.5 |
| 3,989,651 | 11/1976 | Lockwood et al. | 260/2.5 |
| 4,040,992 | 8/1977 | Bechara et al. | 260/2.5 |
| 4,101,465 | 7/1978 | Lockwood et al. | 260/2.5 |
| 4,136,240 | 1/1979 | Zimmerman et al. | 260/2.5 |
| 4,186,255 | 1/1980 | Klein et al. | 521/128 |
| 4,293,680 | 10/1981 | Mazanek et al. | 528/67 |

OTHER PUBLICATIONS

Kresta et al., "Cyclic Sulfonium Zwitterions", (ACS Symp. Ser. 1981), *Anionic Polymerization*, pp. 501–512.

*Primary Examiner*—John M. Ford
*Attorney, Agent, or Firm*—William D. Sabo

[57] ABSTRACT

A process for trimerizing organic polyisocyanates using a select catalyst comprising a quaternary ammonium carboxylic acid salt and a carboxylic acid halide or anhydride. The trimerization products are especially suitable for use in the preparation of polyurethane molding compositions.

14 Claims, No Drawings

PROCESS FOR TRIMERIZING ORGANIC POLYISOCYANATES

This invention relates to a catalytic process for the trimerization of organic polyisocyanates. More particularly, the process involves the use of a select catalyst which includes a quaternary ammonium carboxylic acid salt and a carboxylic acid halide or anhydride.

The trimerization of organic polyisocyanates to form isocyanurates is well known in the art. It is also known to use isocyanurates in the preparation of polyurethane resins to impart improved heat stability as well as other desired properties.

In the trimerization of organic polyisocyanates, many catalysts have been disclosed, including tertiary amines, alkali metal salts of alkanoic acids, quaternary ammonium carboxylate salts, and so forth. Various catalyst combinations have also been employed. U.S. Pat. No. 3,989,651, for instance, discloses the use of N,N-dimethylcyclohexylamine and a tetra (lower-alkyl) quaternary ammonium salt of an alkanoic acid in the preparation of polyisocyanurate spray foams. Exemplificative of other patents which show the state of the art are the following: U.S. Pat. Nos. 3,954,684; 3,980,594; 4,040,992: 4,401,465; 4,136,240; and 4,186,255.

In certain applications, however, it is required that the mixture of polyisocyanate and trimerization products be soluble in organic solvents. One such application involves the use of the mixture in forming a polyurethane which in turn can be cured with free radical generating catalysts to form thermosetting resins. In accordance with this approach, the curing step is typically carried out in the presence of a copolymerizable solvent such as styrene. In using the catalysts and catalyst combinations known in the art, a problem is presented in that there is formed a substantial amount of higher molecular weight product, a significant portion of which is not soluble in styrene or other commonly used solvents.

Now, according to the process of the present invention, it has been found that organic polyisocyanates can be trimerized to form isocyanurate structures which are soluble in conventional organic solvents by employing as the isocyanurate group formation catalyst a select combination of a quaternary ammonium carboxylic acid salt and a carboxylic acid halide or anhydride.

According to the process of the present invention, the isocyanurate group formation catalyst is mixed with an organic polyisocyanate to be trimerized. In carrying out the process, there are generally employed from about 0.1 to about 10 mmoles of the quaternary ammonium carboxylic acid salt per mole of the organic polyisocyanate and from about 0.2 to about 3 mmoles of the carboxylic acid halide or anhydride per mmole of the quaternary ammonium carboxylic acid salt. Preferably, the catalyst includes from about 0.4 to about 4 mmoles of the quaternary ammonium carboxylic acid salt per mole of the organic polyisocyanate and from about 0.4 to about 1 mmole of the carboxylic acid halide or anhydride per mmole of the quaternary ammonium carboxylic acid salt.

In carrying out the process of the invention, any organic polyisocyanate, including pure and crude compositions, which is susceptible to trimerization can be used. These include alkyl polyisocyanates having up to about 10 carbon atoms and aryl, cycloalkyl, aralkyl and alkaryl polyisocyanates having up to about 30 carbon atoms. Typical examples include ethylene diisocyanate, hexamethylene diisocyanate, toluene diisocyanate, phenylene diisocyanate, methylene bis(cyclohexylisocyanate), cyclohexylene diisocyanate, naphthalene diisocyanate, tolyl triisocyanate, methane tris(phenylisocyanate) including all isomers and mixtures thereof. In a preferred embodiment of the invention, there is employed an isomeric mixture of 2,4- and 2,6-toluene diisocyanate in which the weight ratio of the 2,4-isomer to the 2,6-isomer is from about 60:40 to about 90:10, and more preferably from about 65:35 to about 80:20.

The quaternary ammonium carboxylic acid salts which are used have the following general formula:

wherein $R_1$ is selected from the group consisting of hydrogen, $C_1$–$C_{18}$ alkyl, $C_6$–$C_{24}$ aryl, $C_5$–$C_{24}$ cycloalkyl, $C_7$–$C_{24}$ aralkyl and $C_7$–$C_{24}$ alkaryl; and $R_2$, $R_3$, $R_4$ and $R_5$ may each be the same as or different from $R_1$ and are independently selected from the group consisting of $C_1$–$C_{18}$ alkyl, $C_6$–$C_{24}$ aryl, $C_5$–$C_{24}$ cycloalkyl, $C_7$–$C_{24}$ aralkyl and $C_7$–$C_{24}$ alkaryl. The quaternary ammonium carboxylic acid salts can be readily prepared by procedures well known in the art. For example, these carboxylic acid salts can be prepared by reacting the appropriate carboxylic acid with the appropriate quaternary ammonium hydroxide as illustrated below in equation (A):

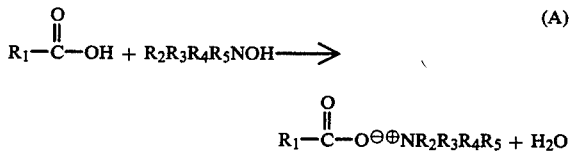

Suitable carboxylic acid reactants include the following and mixtures thereof: formic acid, acetic acid, propionic acid, butyric acid, isobutyric acid, pentanoic acid, hexanoic acid, heptanoic acid, octanoic acid, stearic acid, octadecanoic acid, 2-methylhexanoic acid, 2-ethylhexanoic acid, benzoic acid, toluic acid, chlorobenzoic acid, phenylacetic acid, and the like. Suitable quaternary ammonium hydroxide reactants include the following and mixtures thereof: tetramethylammonium hydroxide, tetraethylammonium hydroxide, tetrabutylammonium hydroxide, tetraoctylammonium hydroxide, trimethylethylammonium hydroxide, tributylethylammonium hydroxide, triethylbutylammonium hydroxide, hexadecyltrimethylammonium hydroxide, benzyltriethylammonium hydroxide, phenyltrimethylammonium hydroxide, and the like.

The quaternary ammonium carboxylic acid salts can also be prepared by reacting the appropriate alkali metal salt of a carboxylic acid with the appropriate quaternary ammonium halide as illustrated below in equation (B):

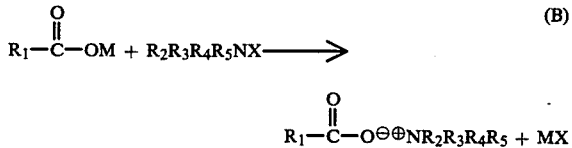

wherein $R_1$, $R_2$, $R_3$, $R_4$ and $R_5$ are as defined above, M is an alkali metal such as Na or K and X is a halogen atom.

Suitable reactants include alkali metal salts derived from the carboxylc acids listed above and quaternary ammonium halide reactants such as the following and mixtures thereof: tetramethylammonium chloride, tetraethylammonium chloride, tetrabutylammonium bromide, tetraoctylammonium chloride, trimethylethylammonium chloride, tributylethylammonium chloride, triethylbutylammonium chloride, hexadecyltrimethylammonium chloride, benzyltriethylammonium chloride, phenyltrimethylammonium hydroxide, and the like.

Any suitable conventional reaction conditions may be employed in the synthesis of the quaternary ammonium carboxylic acid salts. Advantageously and preferably, the reactions in equation (A) and in equation (B) are performed by employing equimolar amounts of the reactants, although a molar excess of either reactant can be suitably employed.

Illustrative quaternary ammonium carboxylic acid salts for use in practicing the process of the invention include the following: tetramethylammonium acetate, tetraethylammonium acetate, tetramethylammonium propionate, tetramethylammonium octanoate, tetramethylammonium 2-ethylhexanoate, tetrabutylammonium 2-ethylhexanoate, benzyltriethylammonium acetate, phenyltrimethylammonium 2-ethylhexanoate, tetrabutylammonium benzoate, and so forth.

Preferred quaternary ammonium carboxylic acid salts include those of the general formula hereinabove wherein $R_1$ is selected from the group consisting of hydrogen and $C_1-C_{18}$ alkyl and $R_2$, $R_3$, $R_4$ and $R_5$ are independently selected from the group consisting of $C_1-C_{18}$ alkyl and $C_7-C_{24}$ aralkyl. In particularly preferred embodiments of the invention, tetrabutylammonium 2-ethylhexanoate and benzyltriethylammonium acetate are employed.

In accordance with the process of the invention, any suitable halide or anhydride which is derived from an aliphatic or aromatic carboxylic acid may be used. Typically, the halide or anhydride compound is obtained from a carboxylic acid reactant containing 2-18 carbon atoms, and more often containing 4-12 carbon atoms. These carboxylic acid reactants include the following and mixtures thereof: aliphatic carboxylic acids, such as acetic acid, propionic acid, butyric acid, valeric acid, caproic acid, lauric acid, stearic acid, and the like; and aromatic carboxylic acids, such as benzoic acid, toluic acid, chlorobenzoic acid, and the like. Carboxylic acid halides are a preferred class of compounds. A particularly preferred carboxylic acid halide is benzoyl chloride.

A wide variety of reaction conditions may be employed in carrying out the trimerization process of the present invention. A solvent is not necessary, but any suitable inert solvent may be employed. Typical examples include the following: cellusolve acetate, ethyl acetate, butyl acetate, acetone, methyl ethyl ketone, methyl isobutyl ketone, ethyl ether, dioxane, benzene, toluene, xylene and dimethylformamide. Furthermore, the reaction temperature and time will both depend upon many factors including the organic polyisocyanate to be trimerized, the exact catalyst being employed, etc. In most situations, the reaction temperature ranges from about 50° to about 120° C. and the reaction time ranges from about 1 hour to about 16 hours. A temperature range of about 80° to about 100° C. is preferred. As the trimerization is highly exothermic, cooling may have to be used in order to maintain the temperature of the reaction mixture within the above-indicated ranges.

It should also be noted that the process can be carried out by mixing the organic polyisocyanate to be trimerized with the reactants used in forming the quaternary ammonium carboxylic acid salt and the carboxylic acid halide or anhydride. In accordance with this embodiment of the invention, the desired quaternary ammonium carboxylic acid salt is generated in situ for use in the trimerization reaction. Other modifications can be made by those skilled in the art without departing from the spirit of the invention.

Employing the select isocyanurate group formation catalyst according to the present invention provides a process which is highly effective in controlling trimerization of an organic polyisocyanate. A mixture is obtained containing unreacted polyisocyanate, trimer, and higher molecular weight trimers and which is virtually completely soluble in common organic solvents. In addition, reproducible results are obtained, as the process is not overly sensitive to variations in catalyst concentrations. Accordingly, using the process of the invention, mixtures are prepared having utility in applications, such as in molding compositions, where solvent solubility is required. These molding compositions are generally employed in a wide variety of utilities such as appliance housings, computer housings, molded electrical parts, and so forth.

The following examples are provided to further illustrate the invention. All parts are by weight unless otherwise specified.

EXAMPLE 1

To 156.74 g (0.9 mole) of diisocyanate① were added 0.35 ml (3.0 mmole) of benzoyl chloride and 1.25 g (3.24 mmole) of tetrabutylammonium 2-ethylhexanoate, and the reaction mixture was then heated to about 55° C. to initiate trimerization. Thereafter, the temperature of the reaction mixture was raised to about 90° C. and then kept at 60°–90° C. for 2½ hours.
①This is a mixture of toluene diisocyanate isomers (80:20 mixture of 2,4/2,6-isomers).

EXAMPLE 2

A mixture of 470 g (2.7 mole) of diisocyanate①, 1 ml (8.6 mmole) of benzoyl chloride, 2.21 g (9.72 mmole) of benzyltriethylammonium chloride, and 0.96 g (9.72 mmole) of finely powdered potassium acetate was heated at about 70° C. to initiate trimerization. After heating overnight, GPC indicated that 30% of the diisocyanate was unreacted.
①This is a mixture of toluene diisocyanate isomers (80:20 mixture of 2,4/2,6-isomers).

EXAMPLE 3

To 174 g (1.0 mole) of diisocyanate① were added 0.01 ml (0.08 mmole) of benzoyl chloride and 0.143 g (0.4 mmole) of tetrabutylammonium 2-ethylhexanoate. The reaction temperature rose to 80° C. over 30 minutes. The reaction mixture was then heated at 90° C. for 5½ hours, and 259 g of styrene was added. After thorough mixing, the styrene solution was decanted; there remained only 0.25 g (0.1%) of styrene insoluble material.
①This is a mixture of toluene diisocyanate isomers (80:20 mixture of 2,4/2,6-isomers).

EXAMPLE 4

A mixture of 174 g (1.0 mole) of diisocyanate① and 0.115 ml (0.8 mmole) of hexanoyl chloride was heated to 75° C., and 0.70 g (2.0 mmole) of tetrabutylammonium 2-ethylhexanoate was then added. The reaction temperature rose to 86° C. over 2 minutes. The reaction mixture was then heated at 90° C. for 4½ hours, and 259 g of styrene was added. After thorough mixing, the styrene solution was decanted; there remained only 0.2 g (0.1%) of styrene insoluble material.

EXAMPLE 5

To 174 g (1.0 mole) of diisocyanate① were added 0.08 ml (0.8 mmole) of acetic anhydride and 0.15 g (0.4 mmole) of tetrabutylammonium 2-ethylhexanoate. The reaction temperature rose to 60° C. over 55 minutes. The reaction mixture was then heated at 90° C. for 4½ hours, and 259 g of styrene was added. After thorough mixing, the styrene solution was decanted, there remained only 0.2 g (0.1%) of styrene insoluble material.
①This is a mixture of toluene diisocyanate isomers (80:20 mixture of 2,4/2,6-isomers).

COMPARATIVE EXAMPLE 1

To 174 g (1.0 mole) of diisocyanate① were added 0.05 ml (0.4 mmole) of benzoyl chloride and 1.43 g (4 mmole) of tetrabutylammonium 2-ethylhexanoate. The reaction temperature rose to 100° C. over 5 minutes. The reaction mixture was then heated at 90° C. for 2 hours, and 259 g of styrene was added. After thorough mixing, the styrene solution was decanted; there remained 6.9 g (4%) of styrene insoluble material.
①This is a mixture of toluene diisocyanate isomers (80:20 mixture of 2,4/2,6-isomers).

COMPARATIVE EXAMPLE 2

To 174 g (1.0 mole) of diisocyanate① were added 0.01 ml (0.08 mmole) of benzoyl chloride and 1.43 g (4 mmole) of tetrabutylammonium 2-ethylhexanoate. The reaction temperature rose to 127° C. over 4 minutes. The reaction mixture was then heated at 90° C. for 2½ hours, and 259 g of styrene was added. After thorough mixing, the styrene solution was filtered, there remained 95.2 g (54%) of styrene insoluble material.
①This is a mixture of toluene diisocyanate isomers (80:20 mixture of 2,4/2,6-isomers).

The composition of the mixtures obtained after trimerization of toluene diisocyanate in the above Examples and Comparative Examples is shown in Table I below. The trimerization of toluene diisocyanate with tetrabutylammonium 2-ethylhexanoate in the presence of benzoyl chloride, as in Example 1, results in a 59.5% conversion of toluene diisocyanate to a mixture of 29% trimer and 30.5% of higher trimers. If the quaternary ammonium salt of the organic acid is generated in situ, as from potassium acetate and benzyltriethylammonium chloride as in Example 2, also in the presence of benzoyl chloride, a similar mixture is obtained. However, the trimerization of toluene diisocyanate with tetrabutylammonium 2-ethylhexanoate with virtually no benzoyl chloride, as in Comparative Example 2, results in a very different mixture: 54% of the reaction mixture is not soluble in styrene.

TABLE I

| Example or Comparative Example (CE) | Quaternary Ammonium Carboxylic Acid Salt (mmoles per mole of diisocyanate) A① | B② | Mole Ratio Carboxylic Acid Halide or Anhydride: Quaternary Ammonium Carboxylic Acid Salt | % Diisocyanate③ | % Diisocyanate Trimer | % Higher Trimers | % Styrene Insoluble |
|---|---|---|---|---|---|---|---|
| 1 | 4 | — | 1 | 40.5 | 29 | 30.5 | 0 |
| 2 | — | 4 | 1 | 34.3 | 21.6 | 44.1 | 0 |
| 3 | 0.4 | — | 0.2 | — | — | — | 0.1 |
| 4 | 2 | — | 0.4 | — | — | — | 0.1 |
| 5 | 0.4 | — | 2 | — | — | — | 0.1 |
| CE-1 | 4 | — | 0.1 | — | — | — | 4 |
| CE-2 | 4 | — | 0.02 | 8.4 | 13.0 | 24.6 | 54 |

① Tetrabutylammonium 2-ethylhexanoate.
② Benzyltriethylammonium acetate, generated in situ from potassium acetate and benzyltriethylammonium chloride.
③ This is a mixture of toluene diisocyanate isomers (80:20 mixture of 2,4/2,6-isomers).

What is claimed is:

1. In a process for trimerizing an organic polyisocyanate in the presence of an isocyanurate group formation catalyst, the improvement which comprises employing as said catalyst from about 0.1 to about 10 mmoles of a quaternary ammonium carboxylic acid salt per mole of said organic polyisocyanate and from about 0.2 to about 3 mmoles of a carboxylic acid halide or anhydride per mmole of said quaternary ammonium carboxylic acid salt, said quaternary ammonium carboxylic acid salt having the formula:

wherein $R_1$ is selected from the group consisting of hydrogen, $C_1$–$C_{18}$ alkyl, $C_6$–$C_{24}$ aryl, $C_5$–$C_{24}$ cycloalkyl, $C_7$–$C_{24}$ aralkyl and $C_7$–$C_{24}$ alkaryl; and $R_2$, $R_3$, $R_4$ and $R_5$ may each be the same as or different from $R_1$ and are independently selected from the group consisting of $C_1$–$C_{18}$ alkyl, $C_6$–$C_{24}$ aryl, $C_5$–$C_{24}$ cycloalkyl, $C_7$–$C_{24}$ aralkyl and $C_7$–$C_{24}$ alkaryl.

2. The process of claim 1, wherein $R_1$ is selected from the group consisting of hydrogen and $C_1$–$C_{18}$ alkyl; and $R_2$, $R_3$, $R_4$ and $R_5$ are independently selected from the group consisting of $C_1$–$C_{18}$ alkyl and $C_7$–$C_{24}$ aralkyl.

3. The process of claim 2, wherein said carboxylic acid salt is tetrabutylammonium 2-ethylhexanoate or benzyltriethylammonium acetate.

4. The process of claim 1, wherein said catalyst includes a carboxylic acid halide.

5. The process of claim 4, wherein said carboxylic acid halide is benzoyl chloride.

6. The process of claim 1, wherein said quaternary ammonium carboxylic acid salt is employed in a proportion from about 0.4 to about 4 mmoles per mole of said organic polyisocyanate.

7. The process of claim 1, wherein said carboxylic acid halide or anhydride is employed in a proportion from about 0.4 to about 1 mmole per mmole of said quaternary ammonium carboxylic acid salt.

8. The process of claim 1, wherein said trimerization is carried out at a temperature of about 80° to about 100° C.

9. The process of claim 1, wherein said organic polyisocyanate is toluene diisocyanate.

10. In a process for trimerizing an organic polyisocyanate in the presence of an isocyanurate group formation catalyst, the improvement which comprises employing as said catalyst from about 0.4 to about 4 mmoles of a quaternary ammonium carboxylic acid salt per mole of said organic polyisocyanate and from about 0.4 to about 1 mmole of a carboxylic acid halide per mmole of said quaternary ammonium carboxylic acid salt, and wherein said trimerization is carried out at a temperature of about 80° to about 100° C., said quaternary ammonium carboxylic acid salt having the formula:

wherein $R_1$ is selected from the group consisting of hydrogen, $C_1$–$C_{18}$ alkyl, $C_6$–$C_{24}$ aryl, $C_5$–$C_{24}$ cycloalkyl, $C_7$–$C_{24}$ aralkyl and $C_7$–$C_{24}$ alkaryl; and $R_2$, $R_3$, $R_4$ and $R_5$ may each be the same as or different from $R_1$ and are independently selected from the group consisting of $C_1$–$C_{18}$ alkyl, $C_6$–$C_{24}$ aryl, $C_5$–$C_{24}$ cycloalkyl, $C_7$–$C_{24}$ aralkyl and $C_7$–$C_{24}$ alkaryl.

11. The process of claim 10, wherein $R_1$ is selected from the group consisting of hydrogen and $C_1$–$C_{18}$ alkyl; and $R_2$, $R_3$, $R_4$ and $R_5$ are independently selected from the group consisting of $C_1$–$C_{18}$ alkyl and $C_7$–$C_{24}$ aralkyl.

12. The process of claim 11, wherein said carboxylic acid salt is tetrabutylammonium 2-ethylhexanoate or benzyltriethylammonium acetate.

13. The process of claim 12, wherein said carboxylic acid halide is benzoyl chloride.

14. The process of claim 13, wherein said organic polyisocyanate is toluene diisocyanate.

* * * * *